United States Patent [19]

Firstenberg et al.

[11] Patent Number: 5,297,566
[45] Date of Patent: Mar. 29, 1994

[54] METHOD AND DEVICE FOR INCREASING THE VOLUME OF A HEAD OF HAIR

[75] Inventors: Donald E. Firstenberg, Edison; Martha L. Huff, Ridgewood; Edward Carhart, Jackson; Donald Warren, Keansburg; Herbert Umstead, Madison; Roland de la Mettrie, Westfield; John A. Penicnak, Mt. Lakes, all of N.J.; Régis Beitone, Paris; Pierre Meurice, L'Isle Adam, both of France

[73] Assignee: L'Oreal, Paris, France

[21] Appl. No.: 736,953

[22] Filed: Jul. 30, 1991

[30] Foreign Application Priority Data

Jul. 31, 1990 [FR] France ................... 90 09748

[51] Int. Cl.$^5$ .............................................. A45D 7/04
[52] U.S. Cl. .................................... 132/203; 132/202; 424/70; 424/71
[58] Field of Search ............... 132/202, 203, 204, 205, 132/207, 209, 210; 424/70, 71

[56] References Cited

U.S. PATENT DOCUMENTS

| | | | |
|---|---|---|---|
| 4,013,787 | 3/1977 | Varlerberghe et al. | 424/71 |
| 4,015,612 | 4/1977 | Pavlik et al. | 424/71 |
| 4,213,960 | 7/1980 | Grollier et al. | 424/70 |
| 4,837,012 | 6/1989 | Kiffel et al. | 424/71 |

FOREIGN PATENT DOCUMENTS

| | | |
|---|---|---|
| 1964794 | 12/1969 | Fed. Rep. of Germany . |
| 2734265 | 7/1977 | Fed. Rep. of Germany . |
| 1582617 | 1/1981 | United Kingdom . |
| 1562560 | 3/1987 | United Kingdom . |

Primary Examiner—Gene Mancene
Assistant Examiner—Frank A. LaViola
Attorney, Agent, or Firm—Cushman, Darby & Cushman

[57] ABSTRACT

The invention relates to a hairdressing method consisting in increasing the apparent volume of a head of hair and simultaneously setting it in this state of swelling by means of an aerosol generator. To do so, the aerosol is shaken with a mass flow of between 0.5 and 4.0 g/s at 20° C., ensuring an atomization which provides a thrust of between 6,500 and 40,000 dynes at 20° C. on a disc having a diameter of 160 mm, placed 150 mm from the dispensing head.

8 Claims, No Drawings

METHOD AND DEVICE FOR INCREASING THE VOLUME OF A HEAD OF HAIR

This invention relates to a hairdressing method consisting in increasing the apparent volume of a head of hair and simultaneously setting it by means of an aerosol spray. The invention also relates to an aerosol generator for implementing this method.

The problem of increasing the apparent volume of a head of hair and then setting it in a state of swelling commonly occurs during hairdressing. Generally, the user, by means of a brush and a hot-air dryer, jointly used, first imparts a certain "swelling" to the head of hair; then, he applies onto the hair a fine spray of a setting product, in order to set the hairstyle in its new "swollen" state. This aerosol spray must be applied in such a way as not to modify the shape of the hair and not to change its style; the aerosol generators presently used for setting the head of hair thus project the dressing aerosol with a minimum force, in order not to disturb the hairstyle in its final state. The above-mentioned hairdressing technique has the disadvantage of being slow and arduous, since it is implemented in two steps, i.e. the swelling, then the setting of the hair.

In the prior art, the brush and the aerosol generator are two different and separate components. From patent U.S. Pat. No. 4,557,619 is also known a device in which a hair brush comprises, in its handle, an aerosol can connected to nozzles which are arranged in the body of the brush and can thus spray the product onto the part of the head of hair worked on by the brush or near to the body of the brush.

The problem the applicants were thinking of is to find a method for imparting to the hair an aesthetical swelling state, in a rapid and easy way, in one technical operation, contrary to what exists in the state of the art using several successive operations.

The solution to this problem consists in producing an aerosol with a sufficient flow to cause the head of hair to swell under the action of the blowing, whilst setting it in this state thanks to the rapid drying of the setting product contained in this aerosol.

Consequently, the object of this invention is a hairdressing method consisting in increasing the apparent volume of a head of hair and simultaneously setting it in this state of swelling, in which there is sprayed into the head of hair an aerosol which is produced by the dispensing head of an aerosol generator, this aerosol being in the form of liquid particles dispersed in a gas or a mixture of propulsive gases, the liquid phase of this aerosol comprising at least one film-forming polymer dissolved in a solvent, which polymer is deposited onto the hair and makes it rigid upon evaporation of said solvent, characterized in that the aerosol is ejected at room temperature with a mass flow between 0.5 and 4.0 g/s at 20° C., ensuring an atomization the ejecting conditions of which correspond to an initial thrust between 6,500 and 40,000 dynes at 20° C., when said atomization acts onto a rigid circular disc having a diameter of 160 mm, with the same axis as the atomization and located at a distance of 150 mm from the dispensing head.

The originality of this invention consists in carrying out, in one single operation, the swelling and the simultaneous setting of the hair, the swelling being caused by the atomizing force and maintained thanks to the dispersion of the dressing polymer throughout the volume of the head of hair and its rapid drying.

In a preferred way, the mass flow of the aerosol generator is between 0.75 and 2.5 g/s. Preferably also, the ejection flow of the aerosol is such that, in the test for measuring the above-defined atomizing force, the initial thrust is between 10,000 and 30,000 dynes.

The invention also concerns a device for the implementation of the process defined above, comprising a pressurized aerosol generator at an initial pressure, at 20° C., between $3.0 \times 10^5$ pascals and $18 \times 10^5$ pascals and fitted with a valve feeding the dispensing head, the aerosol generator containing a propulsive agent and a liquid concentrate containing at least one film-forming polymer, which device is characterized in that the valve, with or without additional gas intake, with a capillary or standard dip tube, associated with the dispensing head, comprises opening of an appropriate size to simultaneously obtain the mass flow and the atomizing force required for the aerosol which allows the implementation of the process.

The propulsive agent is a gas or a mixture of gases selected among the non-liquefied compressed gases, such as air, nitrogen, nitrous oxide and carbon dioxide, or among the liquefied gases, such as the hydrocarbons, the halogenated hydrocarbons or dimethyl ether and their mixtures.

Preferably, the propulsive agent is selected among the group of the liquified gases.

Preferably, the liquid concentrate containing the film-forming polymer(s) for setting hair comprises a solvent taken within the group formed by ethanol, water, methylene chloride, 1,1,1-trichloroethane, isopropanol, acetone, the liquid alkanes (comprising a number of carbon atoms higher or equal to five) and their mixtures. The percentage of these solvents which are less volatile than the propulsive agent makes it possible to adjust the drying time of the atomized composition as well as possible. If the film forming polymers(s) has (have) acid or basic groups, the liquid concentrate containing the polymer(s) for the dressing of the hair contains, in addition, at least one neutralizing agent.

In a preferred embodiment, the aerosol formula contains in solution 1 to 6 weight percent of film-forming polymer(s) for the setting of hair. The particularly suitable film-forming polymer(s) are in particular prepared from the following products: polyvinylpyrrolidone, polystyrene sulphonate, polyethyloxazoline, vinyl acetate/crotonic acid/vinyl t-butyl benzoate, vinylpyrrolidone/vinyl acetate, vinylpyrrolidone/acrylate, vinyl acetate/crotonic acid, vinyl acetate/crotonic acid/vinyl neodecanoate, octylacrylamide/acrylate, octylacrylamide/acrylate/butylaminoethyl methacrylate, acrylate/acrylamide, vinylpyrrolidone/vinyl acetate/vinyl propionate, vinylcaprolactam/vinylpyrrolidone/dimethylaminoethyl methacrylate copolymers or (lower) alkyl ester of the vinyl methyl ether and maleic anhydride copolymer.

The liquid concentrate may contain, in addition, the following usual additives:

1) neutralizing agent, such as soda, potash, monoethanolamine, triethanolamine, 2-amino-2-methyl-1,3-propanediol, 2-amino-2-methyl-1-propanol, triisopropanolamine, some of the above-mentioned alkanolamines, moreover, themselves acting as a plasticizer;

2) plasticizers, such as esters (isopropyl, ethyl or methyl esters of adipic, phthalic, sebacic, and myristic acids), polyols (glycerol, diethylene glycol, dipropylene glycol), silicone oils, glycol ethers (cellosolve, carbitol); lanolin, 3) brillianting or softening additives, such as lanolin derivatives, polyoxyethylenated lanolin, lanolin alcohols, acetylated lanolins;
4) perfumes;
5) protein hydrolysates;
6) vitamins (vitamins B2, B6, E, panthenol);
7) UV filters.

In order to make the object of the invention better understood, some embodiments and examples of implementation will be described below, merely as an illustration and without being exhaustive.

For each example, the aerosol atomization force has been tested at a temperature of 20° C., as follows:

First of all, a device for measuring the aerosol atomization force is made by fixing at a height onto a support, arranged on a horizontal working plane, a precision tensometer having, for instance, a resolution of 100 dynes and a measuring range ranging from 0 to $10^6$ dynes. The tensometer is fitted with a short cylindrical measuring rod which is arranged in a horizontal plane. Onto the end of this rod is fixed a thin solid circular disc with a diameter of 160 mm, so that the axis of the disc coincides with the axis of the rod. The tensometer is connected to a recorder to make it possible to follow the change in the force measured as a function of time. On the same horizontal plane is arranged a movable support having a vertically movable horizontal tray; on this tray is arranged the aerosol generator the aerosol atomizing force of which one wants to measure, so that the outlet opening of the dispensing head is arranged on the axis of the disc, at a distance of 150 mm from this disc. Then the dispensing head of the aerosol generator is pressed for 3 seconds and the maximum value measured by the tensometer is read.

EXAMPLE 1

In a 405 cm$^3$ aerosol receptacle capable of withstanding an internal pressure of $18 \times 10^5$ pascals is placed a charge of 210 g of an aerosol formula formed by the mixture of 67 weight percent of a liquid concentrate J and a liquid propulsive agent comprising 10.5 weight percent of propane and 22.5 weight percent isobutane, the percentages being related to the total weight of the aerosol formula. The liquid concentrate J contains a film-forming polymer R originating from 65 weight percent of vinyl acetate, 10 weight percent of crotonic acid and 25 weight percent of vinyl t-butyl benzoate. The polymer R is prepared according to the method described in example 19 of patent BE 879,602. The liquid concentrate J has the following weight composition:

| Polymer R | 5.33% |
|---|---|
| 2-amino-methyl-1-propanol | 0.57% |
| Water | 3.33% |
| Ethanol, sufficient amount for | 100% |

The internal pressure, measured at a temperature of 20° C., by opening the valve onto a pressure sensor, is $4.9 \times 10^5$ pascals. The can comprising a valve of the "NS-31" type marketed by the "Seaquist Valve" Corporation. This valve is fitted with a dip tube having an inner diameter of 4.2 mm. This valve comprises an additional circular gas-intake opening with a diameter of 1.14 mm and a nozzle comprising two circular feed openings, each opening having a diameter equal to 0.76 mm. The opening of the valve body has an inner diameter of 0.89 mm. The distribution head comprises an outlet opening with a diameter of 1.0 mm.

The way of using the aerosol generator defined above is as follows: a person having a luxuriant head of hair is chosen; the hand-held aerosol generator is brought near the head, at a distance of between 5 and 20 cm from the scalp. Then the dispensing head is firmly pressed for 5 to 20 seconds, whilst atomizing the aerosol throughout the head of hair by moving the device around the head. By weighing, afterwards, the aerosol generator, it is estimated that, during these 5 to 20 seconds, 10 to 45 g of the composition has been ejected out. It is observed that the head of hair of the person has substantially gained in body and that the head of hair "remains" in this swollen state.

A full aerosol generator, such as the one defined above, was subjected to the test for measuring its aerosol atomizing force; the thrust force was 25,000 dynes.

The examples 2 to 16 have been carried out with the same single aerosol generator comprising the following characteristics:

Internal volume of the aerosol receptacles: 405 cm$^3$
Initial charge of the aerosol generator: 210 g
Dispensing head: 1 opening with a 1.02 mm diameter
Valve:
Nozzle: 4 holes with a 0.61 mm diameter
Body: internal restriction of 1.27 mm
Additional gas intake: 0.80 mm diameter
Dip tube: inner diameter: 1.5 mm In examples 2 to 16, all proportions in percentages are given on a weight basis.

EXAMPLE 2

A liquid concentrate with the following formulation is prepared:

| | |
|---|---|
| Vinyl acetate/crotonic acid copolymer sold by the "BASF" Corporation under the name "LUVISET CA 66" | 10 g |
| Plasticizer | 1 g |
| Perfume | 0.02 g |
| Ethanol, sufficient amount | 100 g |

The aerosol generator is filled with 30% liquid concentrate and 70% dimethyl ether. The polymer content in the end product is 3.0%.

This formulation is implemented as indicated in example 1. The result achieved on the head of hair similar.

EXAMPLE 3

A liquid concentrate having the following formulation is prepared:

| | |
|---|---|
| Vinyl acetate/crotonic acid/vinyl neodecanoate copolymer, sold by the "NATIONAL STARCH" Corporation under the name "Resyn 28-2930" | 10 g |
| Water | 43 g |
| Perfume | 0.02 g |
| Ethanol, sufficient amount for | 100 g |

The aerosol generator contains 35% liquid concentrate and 65% dimethyl ether. The polymer content in the end product is 3.5%.

This formulation is implemented as indicated in example 1. The result achieved o the head of hair is similar.

EXAMPLE 4

A liquid concentrate having the following formulation is prepared:

| | |
|---|---|
| Polyethyloxazoline, sold by the "DOW CHEMICAL" Corporation under the trade name "PEO 50 000" | 5 g |
| Perfume | 0.02 g |
| Water, sufficient amount for | 100 g |

The aerosol generator contains 30% liquid concentrate and 70% dimethyl ether. The polymer content in the end product is 3.5%.

This formulation is implemented as indicated in example 1. The result achieved on the head of hair is similar.

EXAMPLE 5

A liquid concentrate having the following formulation is prepared:

| | |
|---|---|
| Butyl half ester of methyl vinyl ether and maleic anhydride copolymer, sold by the "GAF" Corporation under the trade name "GANTREZ ES 425" | 5 g |
| Triisopropanolamine, sufficient amount for 20% neutralization | |
| Plasticizer | 0.5 g |
| Perfume | 0.02 g |
| Ethanol, sufficient amount for | 100 g |

The aerosol generator is filled with 60% liquid concentrate and 40% monochlorodifluoromethane. The polymer content in the end product is 3%.

This formulation is implemented as indicated in example 1. The result achieved on the head of hair is similar.

EXAMPLE 6

A liquid concentrate having the following formulation is prepared:

| | |
|---|---|
| Ethyl acrylate/acrylamide/acrylic acid copolymer sold by the "BASF" Corporation under the trade name "ULTRA HOLD 8" | 6 g |
| 2-amino 2-methyl 1-propanol, sufficient amount for 80% neutralization | |
| Perfume | 0.02 g |
| Ethanol, sufficient amount for | 100 g |

The aerosol generator is filled with 50% liquid concentrate, 30% monochlorodifluoromethane and 20% dimethyl ether. The polymer content in the end product is 3%.

This formulation is implemented as indicated in example 1. The result achieved on the head of hair is similar.

EXAMPLE 7

A liquid concentrate having the following formulation is prepared:

| | |
|---|---|
| Octylacrylamide/acrylate copolymer sold by the "NATIONAL STARCH" Corporation under the trade name "VERSACRYL 55" | 6 g |
| Potassium hydroxide, sufficient amount for 100% neutralization | |
| Plasticizer | 0.6 g |
| Perfume | 0.02 g |
| Ethanol, sufficient amount for | 100 g |

The aerosol generator is filled with 50% liquid concentrate, 30% monochlorodifluoromethane and 20% of a mixture of propane/isobutane/n-butane (20/57/23). The polymer content in the end product is 3%.

This formulation is implemented as indicated in example 1. The result achieved on the head of hair is similar.

EXAMPLE 8

A liquid concentrate having the following formulation is prepared:

| | |
|---|---|
| Vinylpyrrolidone/vinyl acetate copolymer sold by the "GAF" Corporation under the trade name "PVP/VAA E 355" | 8 g |
| Perfume | 0.02 g |
| Ethanol, sufficient amount for | 100 g |

The aerosol generator is filled with 40% liquid concentrate and 60% 1,1,1,2-tetrafluoro ethane. The polymer content in the end product is 3.2%.

This formulation is implemented as indicated in example 1. The result achieved on the head of hair is similar.

EXAMPLE 9

A liquid concentrate having the following formulation is prepared:

| | |
|---|---|
| Vinylpyrrolidone/vinyl acetate/vinyl propionate copolymer sold by the "BASF" Corporation under the trade name "LUVISCOL FC 343E" | 5 g |
| Plasticizer | 0.5 g |
| Perfume | 0.02 g |
| Ethanol, sufficient amount for | 100 g |

The aerosol generator is filled with 60% liquid concentrate, 20% monochlorodifluoromethane and 20% 1,1,1,2-tetrafluoro ethane. The polymer content in the end product is 3%.

This formulation is implemented as indicated in example 1. The result achieved on the head of hair is similar.

EXAMPLE 10

A liquid concentrate having the following formulation is prepared:

| | |
|---|---|
| Octylacrylamide/acrylate/butylaminoethyl methacrylate copolymer sold by the "NATIONAL STARCH" Corporation under the trade name "AMPHOMER" | 6 g |
| 2-amino 2-methyl 1-propanol, sufficient amount for 100% neutralization | |
| Perfume | 0.02 g |
| Ethanol, sufficient amount for | 100 g |

An aerosol generator is filled with 50% liquid concentrate, 30% 1,1,1,2-tetrafluoro ethane and 20% of a mixture of propane/isobutane/n-butane (20/57/23). The polymer content in the end product is 3%.

This formulation is implemented as indicated in example 1. The result achieved on the head of hair is similar.

EXAMPLE 11

A liquid concentrate having the following formulation is prepared:

| | |
|---|---|
| Vinylcaprolactane/vinylpyrrolidone/ dimethylaminoethylmethacrylate sold by the "GAP" Corporation under the trade name "Gaffix VC 713" | 8 g |
| Plasticizer | 0.8 g |
| Perfume | 0.02 g |
| Ethanol, sufficient amount for | 100 g |

An aerosol generator is filled with 40% liquid concentrate and 60% dichlorofluoromethane. The polymer content in the end product is 3.2%.

This formulation is implemented as indicated in example 1. The result achieved o the head of hair is similar.

EXAMPLE 12

A liquid concentrate having the following formulation is prepared:

| | |
|---|---|
| Vinyl acetate/crotonic acid copolymer sold by the "NATIONAL STARCH" Corporation under the trade name "RESYN 28-1310" | 10 g |
| 2-amino 2-methyl 1-propanol, sufficient amount for 100% neutralization | |
| Plasticizer | 1 g |
| Perfume | 0.02 g |
| Ethanol, sufficient amount for | 100 g |

An aerosol generator is filled with 30% liquid concentrate, 20% trichlorodifluoromethane and 50% dichlorodifluoromethane. The polymer content in the end product is 3%.

This formulation is implemented as indicated in example 1. The result achieved on the head of hair is similar.

EXAMPLE 13

A liquid concentrate having the following formulation is prepared:

| | |
|---|---|
| Vinyl acetate/crotonic acid/vinyl neodecanoate copolymer sold by the "NATIONAL STARCH" Corporation under the trade name "RESYN 28-2913" | 5 g |
| Plasticizer | 0.5 g |
| Perfume | 0.02 g |
| Ethanol, sufficient amount for | 100 g |

An aerosol generator is filled with 50% liquid concentrate, 40% dichlorodifluoromethane and 10% of a mixture of propane/isobutane/n-butane (20/57/23). The polymer content in the end product is 3%.

This formulation is implemented as indicated in example 1. The results achieved on the head of hair is similar.

EXAMPLE 14

A liquid concentrate having the following formulation is prepared:

| | |
|---|---|
| Vinyl octylacrylamide/acrylate copolymer sold by the "NATIONAL STARCH" Corporation under the trade name "VERSACRYL 55" | 8 g |
| Potassium hydroxide, sufficient amount for 100% neutralization | |
| Plasticizer | 0.8 g |
| Perfume | 0.02 g |
| Ethanol, sufficient amount for | 100 g |

The aerosol generator is filled with 40% liquid concentrate and 60% 1,1-difluoro ethane. The copolymer content in the end product is 3.2%.

This formulation is implemented as indicated in example 1. The result achieved on the head of hair is similar.

EXAMPLE 15

A liquid concentrate having the following formulation is prepared:

| | |
|---|---|
| Vinylpyrrolidone/vinyl acetate copolymer sold by the "GAF" Corporation under the trade name "PVP/VA E 355" | 6 g |
| Perfume | 0.02 g |
| Ethanol, sufficient amount for | 100 g |

The aerosol generator is filled with 55% liquid concentrate, 31.5% 1,1-difluoro ethane and 13.5% isobutane. The polymer content in the end product is 3.3%.

This formulation is implemented as indicated in example 1. The result achieved on the head of hair is similar.

EXAMPLE 16

A liquid concentrate having the following formulation is prepared:

| | |
|---|---|
| Vinylcaprolactane/vinylpyrrolidone/ dimethylaminoethyl methacrylate copolymer sold by the "GAF" Corporation under the trade name "GAFFIX VC 713" | 6 g |
| Plasticizer | 0.6 g |
| Perfume | 0.02 g |
| Ethanol, sufficient amount for | 100 g |

The aerosol generator is filled with 55% liquid concentrate, 36.9% 1,1-difluoro ethane and 8.1% n-butane. The polymer content in the end product is 3.3%.

This formulation is implemented as indicated in example 1. The result achieved on the head of hair is similar.

We claim:

1. A hairdressing method for increasing the apparent volume of a head of hair and simultaneously setting said head of hair, said method consisting of spraying into said head of hair an aerosol which is produced by a dispensing head of an aerosol generator and is in the form of liquid particles dispersed in a gas or a mixture of propulsive gases, the liquid phase of said aerosal comprising at least one film-forming polymer dissolved in a solvent, which polymer is deposited onto the hair and makes said hair rigid upon evaporation of said solvent, said aerosol being ejected onto said head of hair at room temperature with a mass flow between 0.5 and 4.0 g/sx at 20° C., thereby ensuring an atomization, the ejection conditions of which correspond to an initial thrust between 6,500 and 30,000 dynes at 20° C., when said atomization acts onto a rigid circular disc having a diameter of 160 mm, with the same axis as the atomization and located at a distance of 150 mm from the dispensing head.

2. Method according to claim 1, wherein the mass flow of the aerosol is between 0.75 and 2.5 g/s at 20° C.

3. Method according to claim 1 or 2, wherein the initial thrust is between 10,000 and 30,000 dynes at 20° C.

4. A device for housing and dispensing an aerosol composition so as to increase the apparent volume of a head of hair, said device comprising in combination an aerosol generator container and an aerosol composition housed therein and pressurized at an initial pressure at 20° C. ranging from $3.0 \times 10^5$ Pascals to $18 \times 10^5$ Pascals, said container being fitted with a dispensing head and a valve for feeding said pressurized aerosol composition to said dispensing head, said valve comprising openings having a size so as to produce, simultaneously, on dispensing said aerosol composition from said container (a) a mass flow of said pressurized aerosol composition ranging from 0.5 to 4.0 g/s at 20° C. and (b) an initial thrust of said pressurized aerosol composition ranging from 6,500 to 30,000 dynes at 20° C., said aerosol composition comprising a propulsive agent and a liquid concentrate containing in solution, in a solvent, from 1 to 6 weight percent of at least one film-forming polymer, said solvent being selected from the group consisting of ethanol, water, methylene chloride, 1,1,1-trichlorethane, isopropanol, acetone, a liquid alkane having a carbon content equal to or higher than 5, and a mixture thereof.

5. The device according to claim 4 wherein the said propulsive agent is a gas or a mixture of gases selected from the group consisting of non-liquified compressed gas and a liquified gas.

6. The device according to claim 4 wherein the said propulsive agent comprises at least one non-liquefied compressed gas selected from the group consisting of air, nitrogen, carbon dioxide and nitrous oxide.

7. The device according to claim 4 wherein the said propulsive agent comprises at least one liquefied compressed gas selected from the group consisting of a hydrocarbon, a halogenated hydrocarbon and dimethyl ether.

8. The device according to claim 7 wherein said liquefied propulsive agent is selected from the group consisting of propane, n-butane, isobutane and their mixtures.

* * * * *